United States Patent [19]

Kalishman

[11] Patent Number: 5,065,753
[45] Date of Patent: Nov. 19, 1991

[54] AIR-MOISTURE GENERATION SYSTEM

[76] Inventor: Calvin Kalishman, 7034 Arbor View La., New Port Richey, Fla. 34653

[21] Appl. No.: 519,157

[22] Filed: May 4, 1990

[51] Int. Cl.⁵ .................... A61M 16/10; A61M 15/00
[52] U.S. Cl. ...................... 128/200.11; 128/203.12; 128/203.14; 128/205.18
[58] Field of Search ............ 128/200.11, 203.12, 128/203.14, 203.16, 202.22, 205.18

[56] References Cited

U.S. PATENT DOCUMENTS

| | | | |
|---|---|---|---|
| 1,170,526 | 2/1916 | Gaither | 128/205.21 |
| 3,105,104 | 9/1983 | Neiss | 128/200.11 |
| 3,804,280 | 4/1974 | van Amerongen et al. | 215/1 C |
| 3,903,216 | 9/1975 | Allan et al. | 261/78 A |
| 3,965,894 | 6/1976 | Fischer | 128/194 |
| 4,407,279 | 10/1983 | Tschernezky | 128/200.11 |
| 4,462,398 | 7/1984 | Durkan et al. | 128/200.14 |
| 4,500,480 | 2/1975 | Cambio, Jr. | 128/200.11 |
| 4,606,866 | 8/1986 | McGlothin et al. | 128/202.22 |
| 4,913,140 | 4/1990 | Onec et al. | 128/203.16 |

Primary Examiner—Edgar S. Burr
Assistant Examiner—Kimberly L. Asher
Attorney, Agent, or Firm—Wolf, Greenfield & Sacks

[57] ABSTRACT

A simple air-moisture generation system is provided which employs a tank holding liquid to a level which leaves an air space, above the liquid. An air compressor is provided for furnishing a source of compressed air to an inlet to the tank, and a metering valve is located in the outlet from said air compressor to control the volume and pressure of the air emanating from the compressor and inputted to the tank. An outlet passage from the tank provides the air-moisture flow, and the system preferably is provided with a switch to disable the air compressor when the liquid drops to a designated level in the tank.

4 Claims, 1 Drawing Sheet

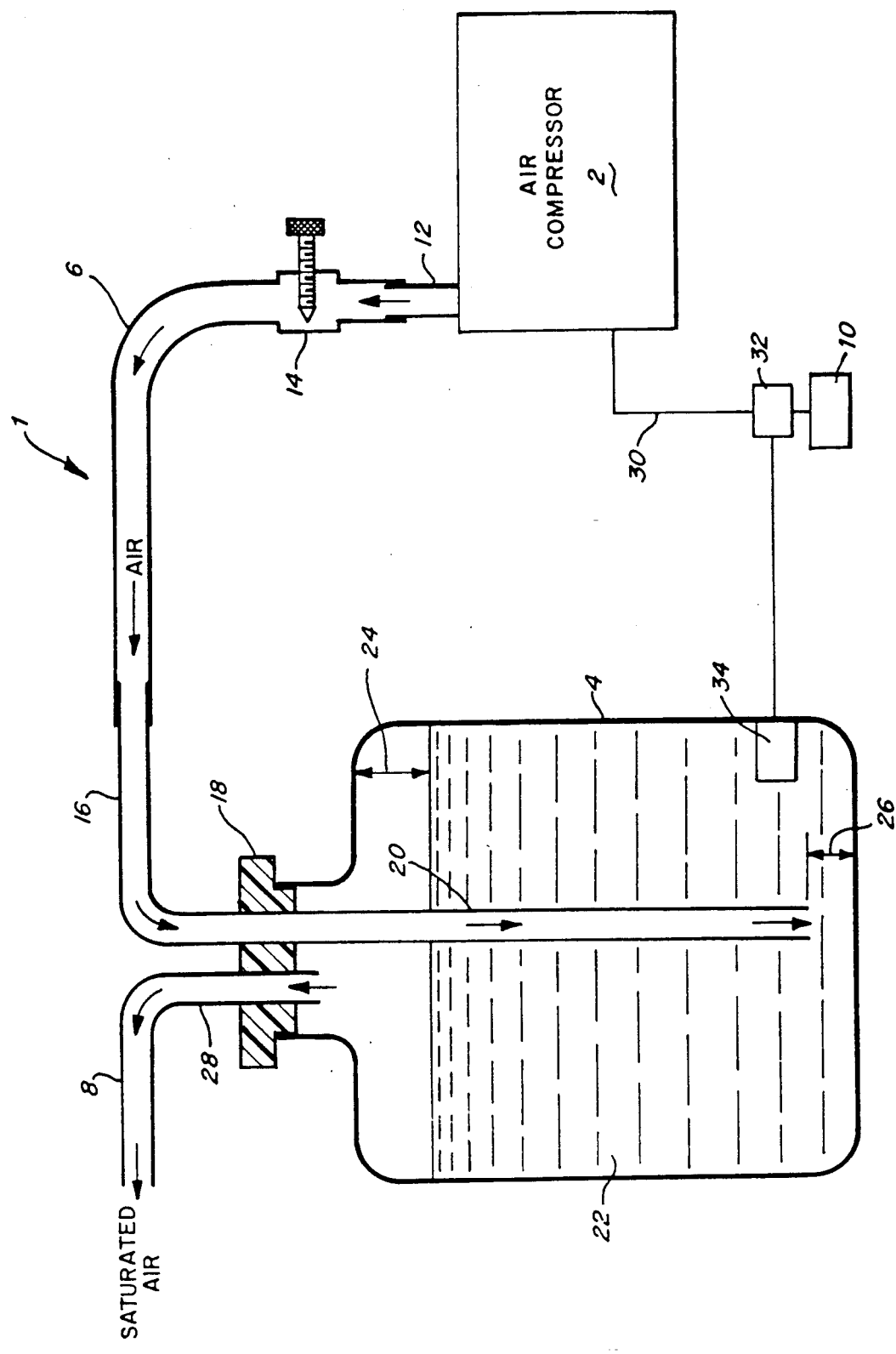

AIR-MOISTURE GENERATION SYSTEM

BACKGROUND OF THE INVENTION

The present invention relates very generally to a system for creating a mixture of air moisture, and more particularly is concerned with providing such mixture for uses such as inhalation therapy or humidification of an air space.

Many devices exist for providing positive pressure inhalation as well as for providing humidification for air in a desired space. Such devices generally involve a number of elements of complex design and substantial cost.

Accordingly, it is an object of the present invention to provide an improved air moisture generation system which is simple in construction and low in cost.

A further object of the present invention is to provide a simplified humidifier which can be controlled with only one valve element and which is manufacturable at low cost.

A still further object of the invention is to provide a system of inhalation therapy in which medicants can be mixed in a tank with water for creating a medicated saturated air mixture for inhalation purposes.

BRIEF DESCRIPTION OF THE DRAWINGS

These and other objects, features and advantages of the invention will become more readily apparent upon a reading of the description following hereinafter and in conjunction with the accompanying drawing, in which:

FIG. 1 illustrates an air-moisture generation system of the present invention.

DETAILED DESCRIPTION

FIG. 1 indicates generally the inhalation system 1. The system comprises an air compressor 2 which may simply be of the fish tank type. The compressor is coupled to a liquid reservoir provided by the tank 4 by means of the air inlet line 6. The tank 4 may simply be a 2-quart container or larger, preferably made of plastic. Leading from the tank is the air outlet line 8.

A power supply 10 is provided to enable operation of the air compressor 2. The air compressor normally is provided with an outlet conduit 12 to which a metering valve 14 is coupled. This metering valve essentially forms a metering jet having a fixed orifice on the order of 0.050-0.060-inch. It has been found that maximum moisture vapor can be created with a relatively small size of metering jet. The metering valve is such as to control to a desired size a restricted opening in the inlet line 6. The size of this restriction is chosen so as to enable reasonable control of pressure and volume of the air flowing in line 6 to enable a desired output to be obtained from the tank 4. The outlet line 6 can of course be of any length and usually is made of plastic material, and terminates in a connection with a rigid tube 16. The tube 16 is passed through an opening in a stopper 18 mounted on the tank 4 and extends into the tank in a straight section 20, which terminates at a distance 26 from the bottom of the tank. The body of the liquid 22 is such that it does not fill the entire tank and leaves an air space 24 above the liquid 22 to provide a storage space for saturated air. The outlet line 8 can also be of any desired length and it terminates in a neck 28 which also passes through the stopper 18 and extends into the air space above the body of liquid.

The device as described is very simple in construction, requiring readily available components. It can be used for a number of purposes such as simply providing a stream of saturated air for humidifying air space. In such case the liquid employed may be distilled water so as to avoid deposition of powder residue on adjacent surfaces.

Alternatively, the system may be employed in inhalation therapy wherein the liquid 22 in the tank can be mixed with medication to treat lung infections. Still further, the system may be used as a deodorizer and accordingly, scented liquid may be employed in the tank 4.

Where it is desired to prevent continuous operation of the air compressor when the liquid is exhausted in the tank 4, there may be provided a float switch 34 which is so located within the tank 4 in relation to the outlet of the straight section 20 of inlet line 6, that when the liquid level drops below a designated point, a signal is created to actuate another switch 32, which normally is closed, and place it in an open circuit position. Accordingly, power will be disrupted in power line 30 to the compressor and it will be shut off. Conversely, when the tank 4 is again filled with liquid, the float switch 34 will operate so as to again close switch 32 and allow the compressor to function.

While a specific embodiment has been shown and described, many variations are indeed possible. Various shaped tanks may be provided and various dimensional changes may be made in order to accommodate the system to any desired configuration.

What is claimed is:

1. An air-moisture generation system comprising:
   a tank for holding a quantity of liquid and having an air inlet and an air outlet means,
   said air inlet means to said tank having a rigid tube extending into said tank and terminating in an outlet at a level spaced from the bottom of said tank,
   an air compressor means for providing a source of compressed air to said air inlet means,
   a switch means located within said tank in a predetermined position with respect to the outlet of said rigid tube which disables said air compressor means when the liquid level falls to a selected level with respect to the rigid tube outlet,
   a metering valve in said air inlet means for controlling the volume of air flowing from said air compressor means into said tank, whereby air under controlled pressure and volume is passed through the liquid in the tank to provide liquid saturated air in the tank,
   said tank having the liquid therein occupying less than the entire volume of the tank to leave a space above the liquid level in which the liquid saturated air is formed,
   and said saturated air is forced out of the outlet means to provide a positive pressure stream of saturated air.

2. The air-moisture system of claim 1 wherein the metering valve has an orifice diameter which does not exceed 0.060-inch.

3. An air-moisture generation system comprising:
   a tank for holding a quantity of liquid and having an air inlet and an air outlet means,
   an air compressor means for providing a source of compressed air to said air inlet means,
   a sensing means for disabling said air compressor means when the liquid level in the tank falls below a predetermined level, said sensing means including means for detecting the liquid level in the tank, and means for controlling said air compressor means responsive to said means for detecting and coupled to said air compressor means, a metering valve in said air inlet means for controlling the volume of air flowing from said air compressor means into said tank, whereby air under controlled pressure and volume is passed through the liquid in the tank to provide liquid saturated air in the tank, said tank having the liquid therein occupying less than the entire volume of the tank to leave a space above the liquid level in which the liquid saturated air in formed, and said saturated air is forced out of the outlet means to provide a positive pressure stream of saturated air.

4. The air-moisture system of claim 3 wherein the metering valve has an orifice diameter which does not exceed 0.060-inch.

* * * * *